United States Patent [19]

Abe et al.

[11] Patent Number: 4,853,546
[45] Date of Patent: Aug. 1, 1989

[54] AUTOMATIC RADIOISOTOPE FILLING APPARATUS

[75] Inventors: Shuzo Abe, Higashi-Kurume; Satoshi Matsunami; Sunao Nagamatsu, both of Tokyo; Masaaki Tanaka; Masao Matsuno, both of Ube, all of Japan

[73] Assignee: Ube Industries, Ltd., Yamaguchi, Japan

[21] Appl. No.: 97,025

[22] Filed: Sep. 16, 1987

[30] Foreign Application Priority Data

Sep. 16, 1986 [JP] Japan .................................. 61-217656
Nov. 12, 1986 [JP] Japan .................................. 61-269365

[51] Int. Cl.⁴ ................................................. G01T 1/16
[52] U.S. Cl. .................................. 250/432 PD; 422/62
[58] Field of Search ..................... 250/432 PD; 422/62

[56] References Cited

U.S. PATENT DOCUMENTS 4,409,488 10/1983 King ............................. 250/432 PD
4,625,118 11/1986 Kriwetz et al. ............... 250/432 PD

FOREIGN PATENT DOCUMENTS

59-51400 3/1984 Japan .

Primary Examiner—Constantine Hannaher
Attorney, Agent, or Firm—Armstrong, Nikaido, Marmelstein, Kubovcik & Murray

[57] ABSTRACT

An automatic radioisotope filling apparatus which includes a radioisotope vial containing a radioisotope solution, a saline vial containing a physiological saline solution and a plurality of label vials containing a drug into which a predetermined amount of the radioisotope solution or the physiological saline solution is to be filled automatically. A required amount of the radioisotope solution or the physiological saline solution is automatically metered and automatically filled into each label vial and consequently the radiation exposure of the operator of the apparatus is minimized.

11 Claims, 6 Drawing Sheets

AUTOMATIC RADIOISOTOPE FILLING APPARATUS

BACKGROUND OF THE INVENTION AND RELATED ART STATEMENT

The present invention relates to an automatic radioisotope filling apparatus for minimizing the radiation exposure of the operator of the apparatus. More particularly, the present invention relates to an automatic radioisotope filling apparatus for minimizing the radiation exposure which the operator of the apparatus undergoes, wherein (a) a radioisotope solution is measured for specific radioactivity, (b) if necessary, the radioisotope solution is diluted with a physiological saline solution to adjust the specific radioactivity to a desired level, then (c) a predetermined amount of the radioisotope solution or the diluted radioisotope solution is automatically filled in a label vial containing a drug.

A drug labeled with an radioisotope (hereinafter referred to as a RI and the drug is hereinafter referred to as a labeled drug), when injected into a human body, is selectively collected in a particular tissue or internal organ of the body, depending upon the type of the labeled drug. Examination of the condition by an appropriate detector makes it possible to obtain the physiological or pathophysiological information of the tissue or internal organ in question.

Many nuclides are used as RIs for labeling. Of them, techneticum 99m (Tc-99m) is used in a largest amount. Tc-99m is a daughter nuclide of Mo-99 and has a short half life of 6 hours. Therefore, Tc-99m is obtained, when required, in a form of a RI solution containing Tc-99m, from an apparatus generally called a technegenerator which contains Mo-99 and its daughter nuclide, namely, Tc-99m and from which only Tc-99m can be taken out selectively. As a matter of course, the specific radioactivity of the RI solution taken out from the technegenerator varies by the time period since the production of the technegenerator or by the producer. Accordingly, the specific radioactivity of the RI solution must be measured correctly in order to prepare a labeled drug of a desired amount. Further, it is necessary in some cases to dilute the RI solution with a physiological saline solution to adjust the specific radioactivity of the former to a desired level.

Preparation of a labeled drug has been manually conducted by measuring the radioactivy intensity of a RI solution contained in a RI vial, separately measuring the amount of the RI solution visually in most cases, calculating the specific radioactivity of the solution from its radioactive intensity and amount both obtained above, and filling a required amount of the RI solution into a vial containing a drug by means of a syringe or the like.

Such manual handling of RI has been defective in that the operator undergoes a large radiation exposure as a result of such an operation over a long period of time and may possibly have a serious hazard.

Hence, Japanese Patent Application Laid-Open No. 51400/1984 disclosed an apparatus wherein the manual handling of RI by operator is improved in order to reduce the radiation exposure the operator undergoes.

According to the apparatus, a predetermined amount of a technetium solution or a physiological saline solution is automatically filled into a label vial containing a drug, from a technetium vial containing the technetium solution or from a saline vial containing the physiological saline solution, by the action of a flow controller provided in the middle of a filling path. Therefore, the apparatus has an advantage of being able to substantially reduce the radiation exposure which the operator undergoes.

However, the apparatus disclosed in Japanese Patent Application Laid-Open No. 51400/1984 is defective in the following points. That is, the apparatus has no stirrer for sufficiently reacting the RI solution filled into the label vial with the drug contained in the vial and therefore the label vial must then be transferred to a separate apparatus for stirring. At this time, the operator cannot avoid radiation exposure. Further, the operator of Japanese Patent Application Laid-Open No. 51400/1984 has no means for measuring the specific radioactivity of the technetium solution in the technetium vial and accordingly the specific radioactivity must be measured and calculated using a separate means before the technetium vial is used in the apparatus. Furthermore, the apparatus accomodates only one label vial and, in preparing a plurality of label vials, it is necessary to remove the label vial which has completed filling and to set a new label vial. This exchange operation induces radiation exposure to the operator and moreover makes the whole operation very complicated.

Hence, the object of the present invention is to provide an automatic RI filling apparatus which can minimize the radiation exposure which the operator of RI solution undergoes.

Other object of the present invention is to provide an automatic RI filling apparatus which can prepare a plurality of label vials continuously.

Still other objects and advantages of the present invention will become apparent from the following descriptions.

SUMMARY OF THE INVENTION

The present invention provides an automatic RI filling apparatus which comprises of a RI vial containing a RI solution, a saline vial containing a physiological saline solution, and a label vial containing a drug into which a predetermined amount of the RI solution or the physiological saline solution is to be automatically filled from the RI vial or the saline vial. This apparatus has a label vial container for accomodating a plurality of the label vials, and into each of these label vials is filled a required amount of the RI solution or the physiological saline solution from the RI vial or the saline vial.

This apparatus preferably has a means for metering the amount of the radioisotope solution taken out of the radioisotope vial by suction, a dilution vial into which said metered amount of the radioisotope solution is to be filled, and a radiation detector for measuring the radioactive intensity of the radioisotope solution filled into the dilution vial. The specific radioactivity of the radioisotope solution filled into the dilution vial is computed from the amount of the radioisotope solution measured by the metering means and the radioactive intensity of the radioisotope solution measured by the radiation detector.

Still further, the apparatus includes a means for metering the amount of the radioisotope solution or the physiological saline solution taken out of the radioisotope vial or the saline vial by suction, a dilution vial into which said metered amount of the radioisotope solution or the physiological saline solution is to be filled, and a radiation detector for measuring the radiation intensity of the solution in the dilution vial. The function of the dilution vial is such that a predetermined amount of the radioisotope solution is metered by the metering means, filled into the dilution vial and measured for radiation intensity and then a predetermined amount of the physiological saline solution is metered by the metering means and filled into the dilution vial containing the radioisotope solution to adjust the specific radioactivity of the radioisotope solution.

DETAILED DESCRIPTION OF PREFERRED EMBODIMENTS

Embodiments of the present invention will be described with reference to the accompanying drawings.

Figure 1:
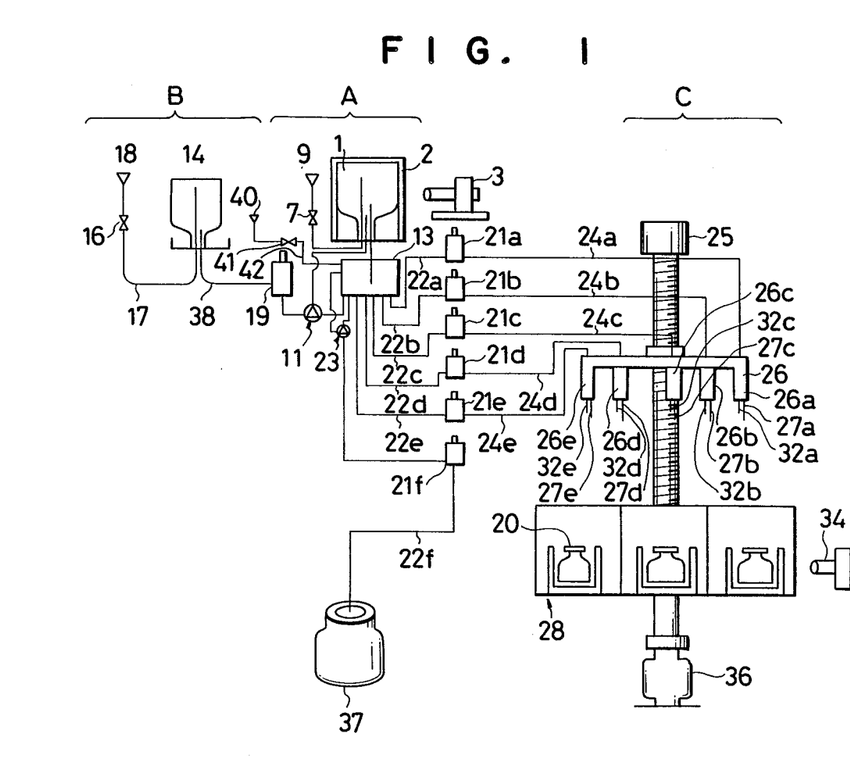
FIG. 1 is a schematic view showing one embodiment of the automatic RI filling apparatus according to the present invention.
Figure 2:
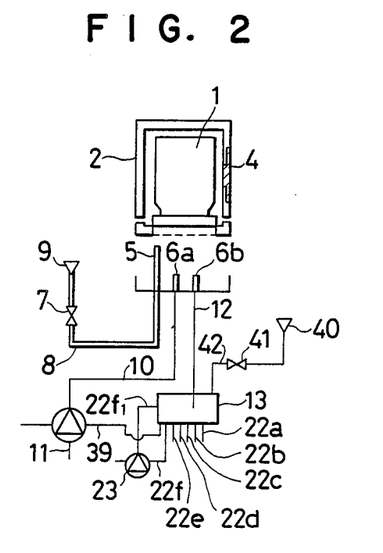
FIG. 2 is a view showing an example of the structure of the technetium vial portion of the apparatus of FIG. 1.

FIG. 1 is a schematic view showing one embodiment of the automatic RI filling apparatus according to the present invention. It consists mainly of a technetium vial portion A, a saline vial portion B and a label vial portion C. In the technetium vial portion A, as shown in FIG. 2, a technetium vial 1 containing a technetium solution is shielded at the outer side by a radiation-shielding member 2 such as lead or the like, and part of the side portion of the radiation-shielding member 2 is a removable cover 4 to enable the measurement of the radioactivity of the technetium solution in the technetium vial 1 by a gamma-ray counter 3. Injection needles 5, 6a and 6b of different lengths are to be inserted into the technetium vial 1 at the bottom. The longer needle 5 is used for air supply. It is connected to an elastic tube 8 having a switching valve 7 in the middle. At the other end of the elastic tube 8 is provided an air filter 9. Of the shorter needles 6a and 6b, 6a is connected to a switching valve 11 via an elastic tube 10 and 6b is connected to a distributor 13 via an elastic tube 12.

Figure 3:
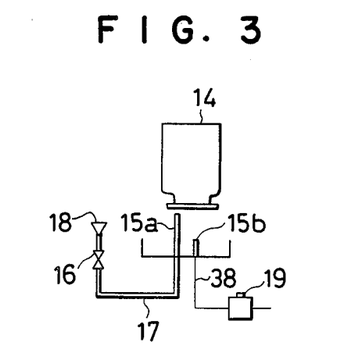
FIG. 3 is a view showing an example of the structure of the saline vial portion of the apparatus of FIG. 1.

In the saline vial portion B, as shown in FIG. 3, injection needles 15a and 15b of different lengths are to be inserted into the saline vial 14 at the bottom. The longer needle 15a is used for air supply. It is connected to an elastic tube 17 having a switching value 16 in the middle. At the other end of the elastic tube 17 is provided an air filter 18. The shorter needle 15b is connected to the switching valve 11 mentioned above via a tube 38 and a plunger 19.

The distributor 13 is connected to plungers 21a, 21b, 21c, 21d, 21e and 21f via tubes 22a, 22b, 22c, 22d, 22e and 22f. The tube 22f has a switching valve 23 in the middle, from which a tube 22f1 is extended and connected to the distributor 13.

To the distributor 13 is also connected an elastic tube 42 having a switching valve 41 in the middle and an air filter 40 at the end.

The operation of the plunger 21f makes the inside of the distributor 13 slightly vacuum, whereby the technetium solution in the technetium vial 1 is drawn into the distributor 13 via the injection needle 6b and the tube 12.

Tubes 24a, 24b, 24c, 24d and 24e extend from the plungers 21a, 21b, 21c, 21d and 21e, respectively, and are connected to downward injection needles 27a, 27b, 27c, 27d and 27e, respectively, which are fixed to arms 26a, 26b, 26c, 26d and 26e of an arm portion 26 of a filling arm mechanism 25. The arm portion 26 is fixed so as to allow a vertical movement. The plungers 21a, 21b, 21c, 21d and 21e supply the technetium solution in respective necessary amounts to label vials 20a, 20b, 20c, 20d and 20e via the tubes 24a, 24b, 24c, 24d and 24e and the injection needles 27a, 27b, 27c, 27d and 27e. The amount of the technetium solution necessary for each of the label vials 20a, 20b, 20c, 20d and 20e can be easily obtained from (a) the radioactivity of the technetium solution in the technetium vial 1 measured by the gamma-ray counter 3 and (b) the radioactivity required for each of the label vials 20a, 20b, 20c, 20d and 20e.

The plunger 21f is not connected to any of the label vials and is connected to a drain 37. It is used for discharging a surplus solution in the distributor 13.

Figure 4:
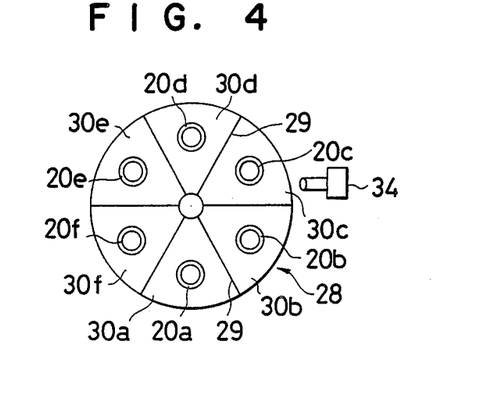
FIG. 4 is a plan view showing an example of the label vial container portion of the apparatus of FIG. 1.

The label vials 20a, 20b, 20c, 20d and 20e and a blank vial 20f are fixed at predetermined positions in a label vial container 28. The label vial container 28, as shown in FIG. 4, is divided into chambers 30a, 30b, 30c, 30d, 30e and 30f whose plan view is of fan shape, by walls 29 radially extending from the center of the container. The label vials 20a, 20b, 20c, 20d and 20e and the blank vial 20f are provided in the chambers 30a, 30b, 30c, 30d, 30e and 30f, respectively.

The blank vial 20f is used for measurement by a gamma-ray counter 34 to obtain a base (blank) data of radioactivity.

Figure 5:
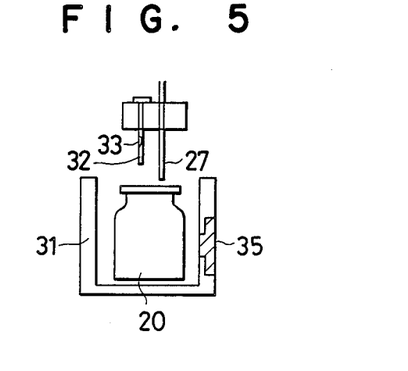
FIG. 5 is a view showing an example of the structure of the label vial portion of the apparatus of FIG. 1.

In the label vial portion C, as shown in FIG. 5, the label vial 20 is surrounded from outside by a radiation-shielding member 31. An injection needle 27 is to be inserted into the label vial 20 from above by the downward movement of the arm portion 26. 32 (actually 32a, 32b, 32c and 32e) is an injection needle having a hole 33 for air removal. Part of the side of the radiation-shielding member 31 is a removable cover 35 for allowing the measurement of the radioactivity in the label vial 20 by the gamma-ray counter 34.

The central shaft of the label vial container 28 is directly connected to a motor 36, whereby the label vials 20a, 20b, 20c, 20d and 20e are subjected, after injection thereinto of the technetium solution or physiological saline solution, to shaking and stirring in order to sufficiently react the drug in each label vial with the injected solution.

In the above embodiment, a motor is used as a stirring mechanism. However, there can also be used other ordinary shaking and stirring mechanisms such as a normally and reversibly rotating mechanism, a seesaw apparatus and the like.

Also in the above embodiment, a removable cover is used for measuring the radioactivity in the technetium vial or each label vial. It can be preferably replaced by a slit-like window. Further, the size ratio of the radiation-shielding member to the vial can be made larger.

Next, the operational examples of the above automatic RI filling apparatus will be described.

Operational Example 1

A. Firstly, the injection needles 5, 6a, 6b, 15a, 15b, 27a, 27b, 27c, 27d, 27e, 32a, 32b, 32c, 32d and 32e, and the tubes 8, 10, 12, 42, 17, 38, 22a, 22b, 22c, 22d, 22e, 22f, 22f1, 39, 24a, 24b, 24c, 24d and 24e are set.

B. The saline vial 14 and the label vial 20 are set. The arm portion 26 of the filling arm mechanism 25 is lowered and the injection needles 27a, 27b, 27c, 27d, 27e, 32a, 32b, 32c, 32d and 32e are inserted into the respective label vials. In needle insertion into the saline vial, the switching valve 16 is closed.

C. The technetium vial 1 is set. The amount of the technetium solution in the technetium vial 1 is input and the radioactivity in the technetium vial 1 is displayed. In needle insertion into the technetium vial 1, the switching valve 7 is closed.

D. The radioactivity required for each of the label vials 20a, 20b, 20c, 20d and 20e is input.

E. Based on the radioactivity in the technetium vial 1, the amount of the technetium solution to be in injected into each label vial is displayed.

F. A start button (not shown) is pushed to start the filling of the technetium solution into each of the label vials 20a, 20b, 20c, 20d and 20e. After the start of the filling, namely, after the start of the operation of the plungers 21a, 21b, 21c, 21d, 21e and 21f, the switching valve 7 is opened.

G. After filling the required amount of the technetium solution, the arm portion 26 is elevated.

H. The radioactivity in each of the label vials 20a, 20b, 20c, 20d and 20e is measured. The radioactivity in the blank vial 20f is also measured.

I. A time for shaking and stirring is input. J. A start button is pushed to start shaking and stirring.

K. After shaking and stirring for a predetermined length of time, the radioactivity in each label vial is measured in the same manner as in H. The results are provided by a printer.

L. The cover 35 of the radiation-shielding member 31 is closed and each label vial is taken out of the container.

Operational Example 2

This example is applied to a case wherein the radioactivity required in each label vial is significantly smaller than that of the technetium solution in the technetium vial and accordingly the dilution of the technetium solution is needed.

A. to E. Same as in A to E in Operational Example 1.

F. A start button is pushed to start the filling of the technetium solution into the label vials requiring no dilution.

G. The switching valve 41 is opened. The solution in the distributor 13 is discharged into the drain 37 by the plunger 21f.

H. As necessary, the saline solution in the saline vial 14 is supplied to the distributor 13 by the plunger 19 via the switching valve 11, and the solution in the distributor 13 is again discharged into the drain 37. After the start of the operation of the plunger 19, the switching valve 16 is opened.

I. The transfer of the physiological saline solution from the saline vial 14 to the technetium vial is started.

J. The radioactivity in the technetium vial 1 is measured and displayed.

K. The filling of the solution in the technetium vial 1 into the label vials requiring dilution is started. After the start of the filling, namely, after the start of the operation of the relevant plungers, the switching valve 7 is opened.

L. The arm portion 26 is elevated after the completion of the filling.

M to Q. Same as H to L in Operational Example 1.

Next, the second embodiment of the present invention will be briefly described with reference to FIG. 6.

A RI vial 101 containing an original RI solution, a syringe 102 as a volume meter consisting of a cylinder and a piston, a saline vial 103 containing a physiological saline solution, and a dilution vial 104 into which the original RI solution or the physiological saline solution is to be filled are connected to each other via a tube 105a. Switching valves 106a, 106b, ... 106l are provided in the middle of the tube 105a. The piston 102b of the syringe 102 can make a linear reciprocating movement by the action of a driving device 107. The radioactivity of a solution in the dilution vial 104 is measured by a radiation detector 115.

In the middle of the tube 105a connecting the RI vial 101 and the syringe 102 is provided a detector 108 for fluid discontinuity which detects abnormality of solution flow in the tube. In the middle of the tube connecting the syringe 102 and the dilution vial 104 is provided a pressure detector 109 for detecting a pressure inside the tube. A tube system consisting mainly of tubes 105 (105a, 105b, ... ) through which solutions or gases flow are fixed on a sheet in one integral tube unit.

Label vials 110a, 110b, 110c, 110d and 110e into which a required amount of a RI solution or a physiological saline solution is to be filled are contained in radiation-shielding lead containers 111c, 111d, 111e, 111f and 111g, respectively. The containers are accomodated in a portable cartridge 112.

Injection needles 118n, 118o, 118p, 118q and 118r inserted into the label vials 110a, 110b, 110c, 110d and 110e, respectively, for supplying or discharging a gas into or from each label vial are connected to tubes 105f, 105g, 105h, 105i and 105j, respectively. The other ends of these tubes are connected to an overflow bag 113. The whole apparatus is controlled by a computer system 114.

In the thus constituted apparatus, before the apparatus is in operation, the dilution vial 104 is empty; the piston 102b of the syringe 102 is pushed down to the bottom of the syringe 102; and all the switching valves 106a, 106b, ... 106l are closed.

When the apparatus is put in operation, the switching valve 106b is opened and then the piston 102b is pulled by predetermined strokes by the driving device 107, whereby a predetermined amount of the original RI solution is collected into the syringe 102 from the RI vial 101. Next, the switching valve 106b is closed, the switching valve 106c is opened, and the piston 102b is pushed down to the bottom of the syringe 102 by the driving device 107, whereby the predetermined amount of the original RI solution is filled into the dilution vial 104. The radioactivity of the original RI solution of known amount filled into the dilution vial 104 is measured by the radiation detector 115. The amount of the solution filled into the dilution vial 104 and the radioactivity measured are input into the computer system 114 by a known method, whereby the radioactivity per unit volume, namely, the specific radioactivity of the RI solution in the dilution vial 104 can be known.

The detector 108 for fluid discontinuity is to examine the presence of a solution in the tube 105a. It is a known detector, for example, a light transmission type sensor. It is used as a means for knowing an end point in transferring the original RI solution in the RI vial 101 to the dilution vial 104 (in this case, the amount of the RI solution from the initial liquid surface to the top end of the injection needle 118a is transferred), or as a means for knowing the shortage of the RI solution in the same transfer.

When the RI solution of known amount and known specific radioactivity in the dilution vial 104 requires dilution for adjusting the specific radioactivity, only the switching valve 106e is opened in a state the piston 102b is at the bottom of the syringe 102 and then the piston 102b is pulled by necessary strokes by the driving device 107, whereby a required amount of the physiological saline solution is collected into the syringe 102 from the saline vial 103.

Next, the switching valve 106e is closed: the switching valve 106c is opened: the piston 102b is pushed down to the bottom of the syringe 102; thereby, the required amount of the physiological saline solution is filled into the dilution vial 104; the RI solution in the dilution vial 104 is diluted: and the specific radioactivity of the RI solution is adjusted.

The pressure detector 109 is a means for detecting whether or not the tubes 105 are appropriately connected to the switching valves 106a to 106l, whether or not these switching valves operate correctly, and whether or not the tube 105a has no leakage. For example, if no required pressure is obtained when (a) a predetermined amount of air is collected into the syringe 102 with only the switching valve 106a opened and (b) the piston 102b is lowered to a desired level with all the switching valves other than 106l closed, it indicates an abnormality.

The second embodiment of the present invention will be described in more detail.

Figure 6:
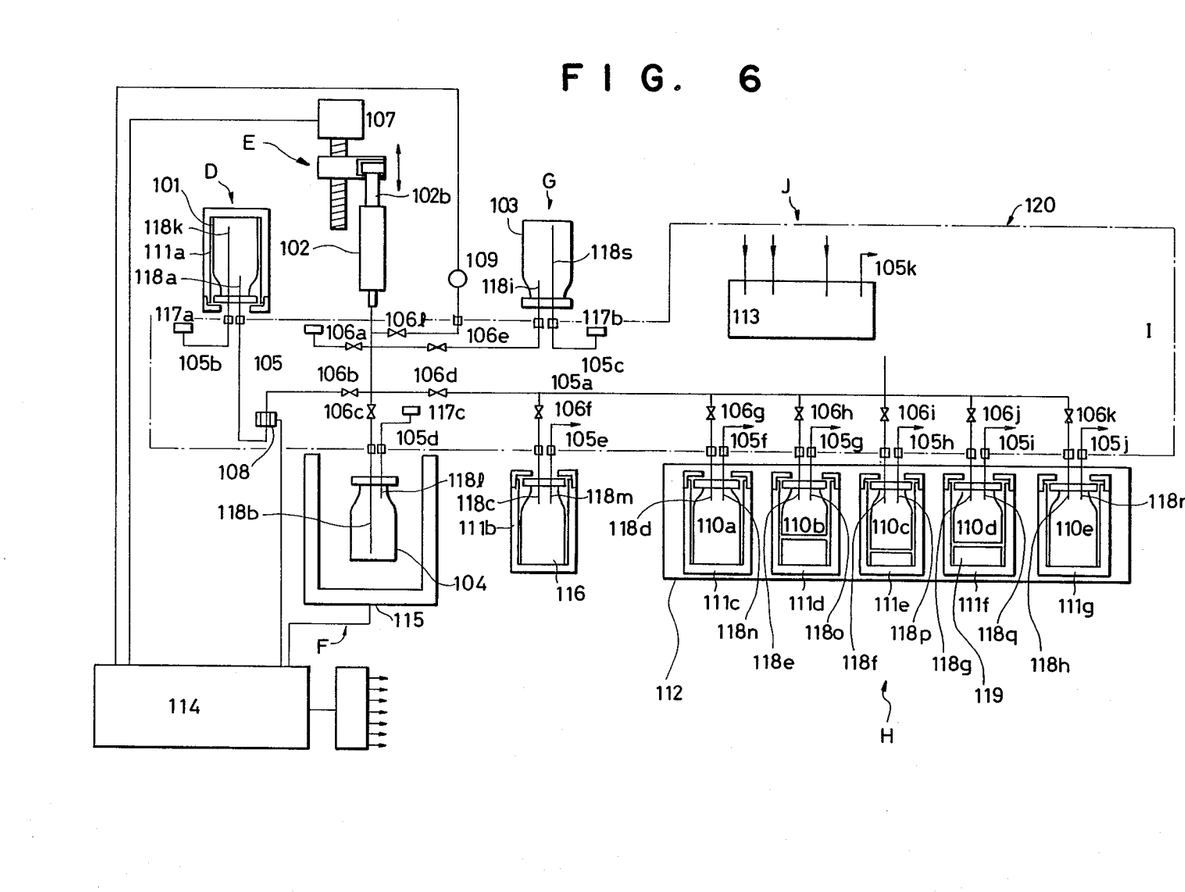
FIG. 6 is a view showing another embodiment of the automatic RI filling apparatus according to the present invention.

FIG. 6 shows a schematic view of the second embodiment of the present invention. This automatic RI filling apparatus consists mainly of a RI vial portion D, a volume metering portion E, a radiation detection portion F, a saline vial portion G, a label vial portion H, a flow path control portion I and an overflow bag portion J.

In FIG. 6, a RI vial 101, a drain vial 116, and label vials 110a, 110b, 110c, 110d and 110e are contained in lead containers 111a, 111b . . . 111g, respectively, for radiation shielding.

Into each vial are inserted injection needles 118a, 118b . . . 118i for injecting a solution, as well as injection needles 118k, 118l . . . 118s for discharging or supplying a gas from or into each vial.

Flow path switching valves 106a, 106b . . . 106l constituting the flow path control portion I allow or stop the flow a solution or a gas in a tube 105a by pressing or relaxing the tube 105a.

The volume metering portion E consists of a syringe 102, a piston 102b (an ordinary syringe is utilized for these syringe and piston), and a driving device 107 for allowing the piston to make a linear reciprocating movement (a pulse motor is used for the device).

The radiation detection portion F consists of a dilution vial 104 and a well-shaped radiation detector 115.

The label vial portion H consists of label vials 110a, 110b . . . 110e, radiation-shielding lead containers 111c, 111d . . . 111g for accomodating the label vials, and a portable cartridge 112 capable of accomodating the lead containers. In the label vials 110a, 110b . . . 110e are inserted injection needles 118d, 118e . . . 118h, respectively, for injecting a solution or a gas. These injection needles are connected to the tube 105a. Into the label vials are also inserted injection needles 118n, 118o . . . 118r for discharging a gas in each label vial. These needles are connected to an overflow bag 113 as a buffer container via tubes 105f, 105g . . . 105j, whereby the contamination of the apparatus in case of the overflow of an solution from each label vial is prevented. The overflow bag 113 is open to the atmosphere via a tube 105k. Into the bottoms of the lead containers 111c, 111d . . . 111g are inserted as necessary spacers 119 so that the heights of the stoppers of each label vial are made same.

In the middle of the tube 105 connecting (a) the injection needle 118a inserted into the RI vial 101 for collecting the original RI solution and (b) the syringe 102, there is provided a detector 108 for fluid discontinuity whch detects the presence of a solution in the tube 105. A tube departs from the middle of the tube connecting the syringe 102 and the dilution vial 104 and is connected to a pressure detector 109 which detects any abnormality in tube system.

The injection needles 118k, 118l and 118m for introducing or discharging a gas into or from the RI vial, the dilution vial and the drain vial are connected to tubes 105b, 105c and 105d, respectively. These tubes are connected to the atmosphere via filters 117a, 117b and 117c.

The RI vial 101 and its lead container 111a, the syringe 102 and its piston 102b, the saline vial 103, the dilution vial 104, the drain vial 116 and its lead container 111b, the tube unit 120 and the cartridge 112 are detachable from a main body of the filling apparatus not shown.

When the filling operation into each label vial is complete, the RI solution remaining in the dilution vial 104 is transferred to the drain vial 116 via the syringe 102.

The automatic RI filling apparatus according to the present invention is controlled by a computer system 114 consisting mainly of a microcomputer or a personal computer and its interfaces with various detectors, various switching valves, the driving device, etc. The main roles of the computer system 114 are (a) acceptance of various set values for operating the system, provided by the operator, (b) control of the driving device 107 for metering of solution volume, (c) computation of specific radioactivity, (d) control of various switching valves necessary for filling of a required amount of the RI solution into the label vials 110a, 110b . . . 110e, (e) control of various operations ordered by instruction buttons not shown and (f) display of computation results or operation status.

Next, the operation of the second embodiment (FIG. 6) of the automatic RI filling apparatus according to the present invention will be described sequentially. A. Required numbers of the label vials 110 are set in the cartridge 112.

The injection needles 118d, 118e . . . for injection into each label vial and for degassing therefrom are set. The label vials 110 into which a solution is filled at once are set in the cartridge 112. (Maximum 5 vials) B. The tube unit 120 is connected to the filling apparatus. The tube 105a is set on pinch valves 116a, 116b . . . The label vial cartridge 112 is set. The injection needles 118d, 118e . . . 118n, 118o . . . of the label vials 110 are connected to the tubes 105a, 105f, 105g . . .

The injection needles 118c and 118b are connected to the drain vial 116 and the dilution vial 104. The dilution vial 104 is set in the well-shaped radiation detector 115. The syringe 102 is connected to the tube 105a and set in the driving device 107. C. Test of leakage and plugging in the switching valves 106a, 106b . . . and in the tubes. The filling apparatus conducts the following actions by pushing the relevant buttons of the computer system 114. (1) All the switching valves 106a, 106b . . . are closed and an air pressure is applied by the syringe 102, whereby leakage is monitored from the value of the pressure sensor. (2) The operation of the switching valves 106a, 106b . . . are tested by monitoring the air pressure through a sequential opening and closing of these valves. D. Input of filling data into the computer system 114

With respect to each label vial, input the desired radioactivity, the volume, the size, the drug amount and the type of nuclide. (1) After the completion of inputting, the computer system 114 computes the volume and specific radioactivity of the RI solution to be filled into each label vial 110. E. The saline vial 103 is set. F. The RI vial 101 taken out of a technegenerator is set. G. Start of filling The filling apparatus conducts the following actions by pushing the relevant buttons of the computer system 114. (1) The original RI solution is transferred from the RI vial 101 to the dilution vial 104 by the suction of the syringe 102. (2) The volume of the original RI solution transferred to the dilution vial 104 is calculated from the cycle of the syringe 102 movement. (3) The radioactivity of the original RI solution in the dilution vial 104 is measured. (4) The original RI solution in the dilution vial 104 is diluted with the physiological saline solution so as to give the highest specific radioactivity required in the label vials 110. (5) The thus diluted RI solution in the dilution vial 104 is metered and filled into one of the label vials 110. (6) A predetermined amount of the physiological saline solution for concentration adjustment and tube inside washing is filled into the above one of the label vials 110. (7) The residual solution in the tube is forwarded into said one of the label vials 110 by air by the reciprocating action of the syringe 102. (8) The above procedures (5) to (7) are repeated with respect to other label vials 110. When a label vial of far lower specific radioactivity than other label vials is required, the once diluted RI solution is further diluted when all other label vials have been filled and this doubly diluted solution is filled. (9) After the completion of filling, the residual solution remaining in each injection needle 118a, 118b . . . is forwarded to the drain vial 116 utilizing the sucking action of the syringe 102. (10) The completion of filling is input into the computer system 114. The details of filling are printed by a printer each time.

Figure 7:
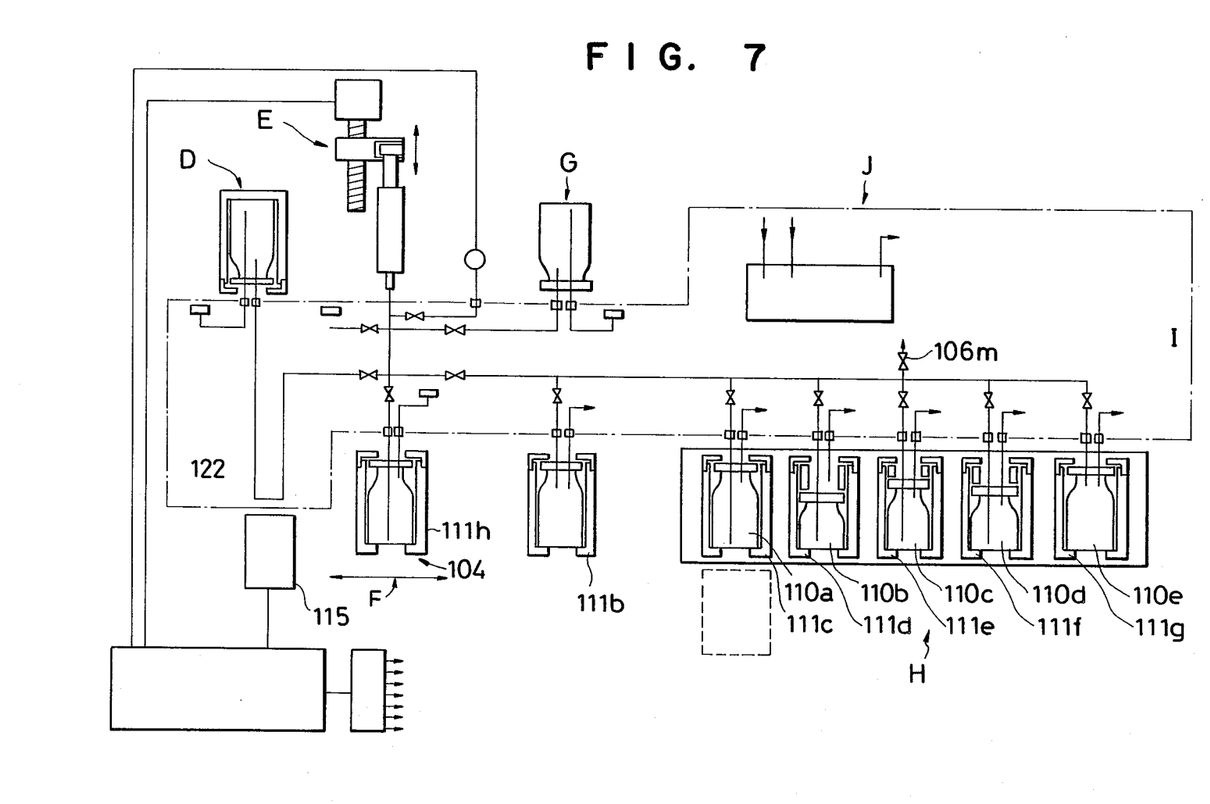
FIG. 7 is a view showing still another embodiment of the automatic RI filling apparatus according to the present invention.

FIG. 7 shows the third embodiment of the automatic RI filling apparatus according to the present invention.

This apparatus differs from the apparatus of the second embodiment in that (a) the radiation detector 115 is movable by the use of a driving mechanism not shown, (b) the lead container 118h containing the dilution vial 104 is detachable and (c) the lead containers 111b, 111c . . . 111h each have a hole at the bottom for enabling the measurement of radioactivity through the hole.

The portions of the operation of the third embodiment which are largely different from the operation of the second embodiment will be described below.

In metering the original RI solution in the RI vial 101 and filling it into the dilution vial 104, the radiation detector 115 is moved to the detector 122 for fluid discontinuity and the abnormality of solution volume in the tube 105 is detected by the change of radioactivity. In measuring the radioactivity in the dilution vial 104, the radiation detector 115 is moved to below the dilution vial 104. After each of the label vials 110a, 110b . . . 110e has been filled with a required amount of the RI solution from the dilution vial 104, the radiation detector 115 is sequentially moved to below these label vials to measure the respective radioactivities.

Figure 8:
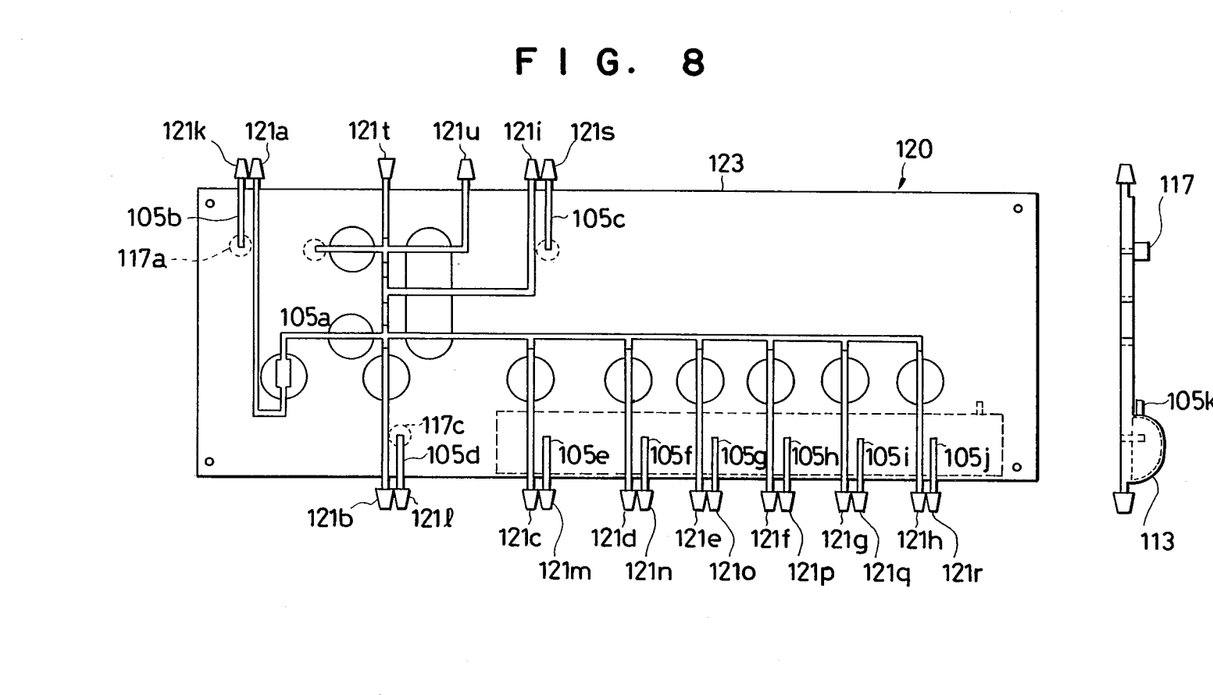
FIG. 8 is a view showing one example of a tube unit of the present apparatus wherein all the tubes are fixed on a sheet in a form of one integral system.

FIG. 8 shows an example of a tube unit 120 wherein most of tubes 105a, 105b . . . have been fixed on a sheet 123 in one integral system in order to make the detachment of these tubes easy.

Joints 121a, 121b . . . 121s are joints with injection needles 118a, 118b . . . 118s. Joints 121t and 121u are joints with a syringe 102 and a pressure detector 109, respectively.

As described above, in the automatic RI filling apparatus of the present invention, filling of RI solution into a plurality of label vials can be conducted automatically; the operation is very easy; and the radiation exposure which the operator of RI solution undergoes can be minimized.

Further in the automatic RI filling apparatus of the present invention, the presence of a syringe for metering of solution volume and a dilution vial enables filling of an original RI solution of known volume into the dilution vial; accordingly the specific radioactivity of the original RI solution can be correctly known by measuring the radioactivity of the original RI solution in the dilution vial; and the specific radioactivity of the original RI solution in the dilution vial can be adjusted by filling a required amount of a physiological saline solution into the dilution vial using said syringe.

Furthermore, the presence of a detector for fluid discontinuity can confirm no occurrence of fluid discontinuity in transferring an original RI solution from a RI vial to a dilution vial and accordingly can obtain the transferred volume of the original RI solution correctly.

Moreover, the presence of a pressure detector in the middle of a tube can detect abnormalities of the tube system such as leakage and the like; and integration of the tubes into one tube unit makes detachment of tubes easy.

In addition, the label vials in a radiation-shielding lead container can be accomodated in a portable cartridge, which makes setting of the label vials in the filling apparatus easy and can minimize radiation exposure during cartridge transfer.

Once setting of RI vial, saline vial and label vials in the filling apparatus is over, the measurement of the specific radioactivity of original RI solution, dilution operation and filling operation of RI solution into label vials are conducted automatically, whereby the radiation exposure which the operator undergoes can be minimized.

What is claimed is:

1. An automatic radioisotope filling apparatus which comprises:
a radioisotope vial containing a radioisotope solution,
a saline vial containing a physiological saline solution, a plurality of label vials containing a drug into which a predetermined amount of the radioisotope solution or the physiological saline solution is to be provided from the radioisotope vial and the saline vial, a container for said plurality of label vials, conduit means for selectively transferring the radioisotope solution and the physiological saline solution from the radioisotope vial and the saline vial to each of the pluraltiy of label vials, and means for selectively and automatically controlling the flow of said radioisotope solution and the physiological saline solution through said conduit means, whereby a required amount of the radioisotope solution and the physiological saline solution for each of the label vials may be automatically withdrawn from the radioisotope vial and the saline vial and provided to each of the label vials.

2. An automatic radioisotope filling apparatus according to claim 1 wherein said container for said plurality of label vials is provided with a stirring mechanism.

3. An automatic radioisotope filling apparatus according to claim 1, wherein said conduit means includes a distributor for receiving said radioisotope solution and said physiological saline solution and directing the flow of said radioisotope solution and said physiological saline solution to each of said plurality of label vials.

4. An automatic radioisotope filling apparatus which comprises:

a radioisotope vial containing a radioisotope solution, a saline vial containing a physiological saline solution, a plurality of label vials containing a drug into which a predetermined amount of the radioisotope solution or the physiological saline solution is to be provided from the radioisotope vial and the saline vial, a dilution vial, conduit means including said dilution vial for selectively transferring the radioisotope solution and the physiological saline solution from the radioisotope vial and the saline vial to each of the plurality of label vials, means for selectively and automatically controlling the flow of said radioisotope solution and the physiological saline solution through said conduit means including, metering means for withdrawing and transferring a measured volume of the radioisotope solution from said radioisotope vial to said dilution vial, a radiation detector for measuring the radioactive intensity of the radioisotope solution transferred to the dilution vial, and means for calculating the specific radioactivity of the radioisotope solution transferred to the dilution vial based on the measured volume and radioactive intensity of the radioisotope solution transferred to the dilution vial.

5. An apparatus for automatically providing a plurality of label vials containing a radioactive solution of a specific radioactivity comprising:

a radioisotope vial containing a radioisotope solution, a saline vial containing a physiological saline solution, a plurality of label vials containing a drug into which said radioisotope solution is to be provided, a dilution vial, conduit means for selectively transferring the radioisotope solution and the physiological saline solution from the radioisotope vial and the saline vial to the dilution vial, metering means for withdrawing and transferring a measured volume of the radioisotope solution from said radioisotope vial to said dilution vial, a radiation detector for measuring the radioactive intensity of the radioisotope solution transferred to the dilution vial, and means for calculating the specific radioactivity of the radioisotope solution transferred to the dilution vial based on the measured volume and radioactive intensity of the radioisotope solution transferred to the dilution vial and determining a volume of the physiological saline solution required to adjust the radioactive intensity of the radioisotope solution in the dilution vial to a specific radioactivity, metering means responsive to said calculating means for withdrawing and transferring said required volume of the physiological saline solution to said dilution vial, and means for selectively transferring the radioisotope solution and physiological saline solution from said dilution vial to said label vials.

6. An automatic radioisotope filling apparatus according to claim 4 or 5, wherein said conduit means includes a plurality of tubes and further comprising a detector for fluid discontinuity provided in the middle of a tube connecting the radioisotope vial and the metering means.

7. An automatic radioisotope filling apparatus according to claim 4 or 5, wherein said conduit means includes a plurality of tubes and further comprising a pressure detector provided in the middle of a tube connecting the metering means and the dilution vial.

8. An automatic radioisotope filling apparatus according to claim 4 or 5, wherein said conduit means includes a plurality of tubes for transferring the radioisotope solution and the physiological solution and for venting gases during transfer of said solutions and said plurality of tubes are fixed for support on a sheet which provides an integral flow unit.

9. An automatic radioisotope filling apparatus according to claim 4 or 5, wherein the label vials are accomodated in a plurality of radiation-shielding lead containers fixed to a portable cartridge.

10. An automatic radioisotope filling apparatus according to claim 4 or 5, wherein a needle is inserted into each label vial for supplying or discharging a gas into or from the label vial, a tube is connected to the needle at one end, and the other end of the tube is connected to a buffer container.

11. An automatic radioisotope filling apparatus according to claim 4 or 5, wherein the label vials are provided with a stirring mechanism.

* * * * *